United States Patent

Stang

(10) Patent No.: US 8,844,538 B2
(45) Date of Patent: Sep. 30, 2014

(54) SURGICAL DRAPE

(75) Inventor: Silke Stang, Heidenheim (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 307 days.

(21) Appl. No.: 13/395,443

(22) PCT Filed: Jun. 28, 2010

(86) PCT No.: PCT/EP2010/003928
§ 371 (c)(1),
(2), (4) Date: Mar. 11, 2012

(87) PCT Pub. No.: WO2011/038792
PCT Pub. Date: Apr. 7, 2011

(65) Prior Publication Data
US 2012/0167896 A1    Jul. 5, 2012

(30) Foreign Application Priority Data

Sep. 30, 2009 (DE) .......................... 10 2009 047 896

(51) Int. Cl.
*A61B 19/08* (2006.01)
*A61B 19/00* (2006.01)

(52) U.S. Cl.
CPC ......... *A61B 19/08* (2013.01); *A61B 2019/5483* (2013.01); *A61B 2019/5272* (2013.01)
USPC ........................................ 128/849; 600/124

(58) Field of Classification Search
CPC .... A61B 19/08; A61B 19/081; A61B 19/087; A61B 19/088; A61B 19/10; A61B 19/12; A61B 2019/08; A61B 2019/081; A61B 2019/10; A61B 2019/103; A61B 2019/106

USPC ...................... 128/849–856; 600/21–22, 119, 600/124–125; 604/355–357; 382/153; 378/203

See application file for complete search history.

(56) References Cited

U.S. PATENT DOCUMENTS

| 4,223,669 A | * | 9/1980 | Morledge | 128/847 |
| 4,275,719 A | * | 6/1981 | Mayer | 128/847 |
| 5,312,385 A | * | 5/1994 | Greco | 604/356 |
| 5,339,831 A | * | 8/1994 | Thompson | 128/852 |
| 5,490,524 A | * | 2/1996 | Williams et al. | 128/849 |
| 5,778,891 A | * | 7/1998 | McMahan | 128/849 |

(Continued)

FOREIGN PATENT DOCUMENTS

| DE | 10 2006 059 163 | 8/2007 |
| EP | 1 641 407 | 4/2006 |
| WO | WO 96/38096 | 12/1996 |

*Primary Examiner* — Patricia Bianco
*Assistant Examiner* — Kari Petrik
(74) *Attorney, Agent, or Firm* — Paul Vincent

(57) ABSTRACT

A surgical drape (10) has a planar, flexible covering element (11) with an area (30) for accommodating a reference means (40) for a navigation system, the reference means protruding from the plane of the covering element. The area (30) has at least two deformable, elongated bar elements (18), which are connected to the covering element (30) and have two bar ends (27). The bar elements include the area (30) for accommodating the reference means (40) between the bar elements. At least one elongated shortening means (20) can be fixed on the covering element (11) and interacts with at least one of the bar elements (18), for reducing and/or fixing the distance of the two bar ends (27) from each other so that the area (30) for accommodating the reference means (40) is lifted out of the plane of the covering element (11).

22 Claims, 3 Drawing Sheets

(56) References Cited

U.S. PATENT DOCUMENTS

| | | |
|---|---|---|
| 2006/0169290 A1 | 8/2006 | Harris |
| 2007/0000498 A1* | 1/2007 | Glynn et al. ............ 128/852 |
| 2007/0175486 A1 | 8/2007 | Bogojevic |
| 2007/0267028 A1* | 11/2007 | Junk ............ 128/849 |
| 2010/0200002 A1* | 8/2010 | Orban, III et al. ............ 128/853 |
| 2010/0275929 A1* | 11/2010 | Kaska ............ 128/852 |
| 2011/0174318 A1* | 7/2011 | Reyes et al. ............ 128/852 |
| 2013/0133670 A1* | 5/2013 | Junk ............ 128/854 |
| 2013/0211425 A1* | 8/2013 | Parsell et al. ............ 606/131 |
| 2013/0274609 A1* | 10/2013 | Glynn et al. ............ 600/467 |

\* cited by examiner

SURGICAL DRAPE

This application is the national stage of PCT/EP2010/003928 filed on Jun. 28, 2010 and claims Paris Convention Priority of DE 10 2009 047 896.5 filed Sep. 30, 2009.

BACKGROUND OF THE INVENTION

The invention relates to a surgical drape, comprising a planar, flexible covering element having an area for accommodating a reference means for a navigation system, the reference means protruding from the plane of the covering element.

The purpose of surgical drapes is to keep an area of surgical intervention clean and sterile. This requires that drapes have openings in the intervention area, wherein so-called incision films can be provided in these areas, in such a way that the operating surgeon has a good view of the field of the operation until the instant of intervention, such as an incision to open the body of the patient, wherein the entire covered surface is sterile.

Moreover, surgical drapes are also known in which a covering means for a reference means that protrudes from the plane of the surface of the drape and is identifiable to a two- or three-dimensional measuring system is accommodated in the area of an opening.

In particular, in the case of neurological surgical interventions on the human body, it is common to measure the exact area of surgical activity before intervention to locate the latter as precisely as possible and to spare healthy tissue. Moreover, during intervention, the results may be intraoperatively verified by the surgeon using computer tomographs or other imaging methods, such as X-rays and MR or the like.

To retain the exact position of the area of surgical activity, which was determined by prior measurement, further or other measuring systems are deployed during the operation that can work both two- and three-dimensionally, e.g. with two infrared sensors and receivers. Because the coordinate reference points for the area of surgical activity change when the navigation system, which may be an identical system or another system, is changed, it is conventional to provide a suitable reference means in the area of the surgical intervention that is identified by the second measuring system.

For example, two- and three-dimensional navigation systems with the corresponding number of, for example, infrared transmitters and receivers are used that comprise a reference means, for example, in the form of a three-point star (also called reference star), wherein the reference star can also be described as a navigation base unit.

This frequently makes it necessary to position the reference means in such a way that it is as sterile as possible, but identifiable to the navigation system. The reference means frequently protrudes from the plane that is covered by the drape and is usually above the intervention area.

Such a navigation system is described, for example, in EP 1 923 015 A1, wherein the corresponding reference means can be attached, for example, to objects, in particular, to medical instruments and to structures of the body.

The drape known from EP 1 641 407 B1 describes a further fenestration area next to the intervention area in which an already preformed hood-like film is used, wherein the reference means can then be deployed in the region of the hood-like film. Further, so-called tapering means are described by which the hood can then be adapted to the shape of the reference means by reducing its volume by drawing together the tapering means such that the hood lies on the structure of the reference means, preferably without folds.

The disadvantage of the described drape is that, even when not in use, the hood-like part, formed by a covering means connected to the drape around the circumference of a second fenestration, protrudes from the plane of the drape or the two elements. The drape and the covering means are therefore stored separately and have to be sterilized separately and are only connected together at the time of operation. However, if the two elements are already connected together it is more difficult to position the drape because the covering means protrudes from the plane of the planar drape, which projects from the drape in a shape resembling a bell.

The object of the invention is to avoid these disadvantages and to provide a surgical drape, in particular for neurological surgical procedures that provides an area for accommodating a reference means for a navigation system, the reference means protruding from the plane of the covering element, and also to permit simple storage of the drape, in particular, storage such that the area of the drape intended to accommodate the reference means is as free of folds and creases as possible. It is also an object of the invention to provide an area that is individually adjustable to each application, for accommodating reference means protruding from the plane of the covering element.

SUMMARY OF THE INVENTION

The invention achieves this object by means of a surgical drape comprising a planar, flexible covering element having an area for accommodating a reference means for a navigation system, the reference means protruding from the plane of the covering element, wherein the area has at least two deformable, elongated bar elements, which are at least partially connected to the covering element and have two bar ends, wherein the bar elements include the area for accommodating the reference means between the bar elements, and which at least one elongated shortening means, which can be fixed on the covering element and interacts with at least one of the bar elements, for reducing and/or fixing the distance of the two bar ends from each other in the plane of the covering element so that the area for accommodating the reference means is lifted out of the plane of the covering element.

An especially advantageous aspect of such a configuration is that, on the surgical drape comprising a planar, flexible covering element, that is the actual drape material for covering the body of a patient, having an area in which, after it has been lifted above the plane of the surface of the covering element, the reference means of a navigation system can be accommodated, this area in which the reference means can be accommodated is also in the plane of the flexible, planar covering elements when in the storage condition, that is, when not in use. This means that, in the unused or non-deformed condition of the bar elements, the surgical drape is a completely planar, flexible web of material comprising, in the same plane, the covering element thereby having an area in which the reference means can later be accommodated Because deformation of the at least two bar elements results in a reduction of their mutual distance between the bar ends, a tunnel-like area is provided between the two bar elements, which are deformed in the shape of an arch and in which the reference means can be accommodated. This is especially advantageous because, due to the tunnel-like shape, an especially smooth hood can be provided that has neither seams nor folds in the area of the reference means so that, for example, the scan function of a camera of the navigation system can advantageously be performed without reflections.

At least two bar elements are provided that are deformable on this covering element, which can have any shape, such as, in particular, square, rectangular, triangular, oval, round, in particular, especially a rectangular shape. The bar elements can either be elastically deformable or, in particular, preferably plastically deformable. Plastically deformable bar elements do not recover their shape, or substantially not their original shape, once the force causing the deformation is removed.

The connection between the bar elements and the covering element is at least partial, wherein, in particular, fixture to the covering element over the entire length of the bar element is preferred. It is basically also possible to connect the bar elements to the covering element, for example, in the area of the two bar ends and in one or more discrete central areas. In particular, the bar elements can be connected to the covering element by means of a plastic coating applied to the former. Alternatively, the bar elements can be fixed on the drape by means of an adhesive. Alternatively, the bar elements can be welded to the drape. Alternatively, the bar elements can also be guided into pockets on the covering element.

The elongated shortening means are used, in particular, to form a limitation, essentially in the plane of the covering element, of the area of the covering element that is lifted out of the plane of the covering element.

The elongated shortening means to reduce and/or fix the distance between the two bar ends from each other in the plane of the covering element can, in particular, be constituted by a textile ribbon element but also by a strip, for example, of adhesive film. The shortening means can be constituted to act as a fastener over its entire length or only in individual areas, in particular, in the two end areas of the elongated shortening means. In principle, fastening is possible both by cohesive and adhesive material. Hook and loop fastening material can also be used.

In particular, the shortening means is already detachably or non-detachably connected to the covering element by one of its ends during storage and before use of the surgical drape while the other end area is either not connected to the covering element or connected to the flexible covering element in a position in which the bar elements are not yet deformed. In particular then, after deformation forces are applied to the bar element to deform the bar element and after the latter has been lifted out of the plane of the covering element, in particular, in the case of a plastically deformable bar element, the deformation of the bar element can be further stabilized by fixing the elongated shortening means to a second fastening element. Alternatively, by fixing the elongated shortening means to a second fastening element, deformation of the, in particular, elastically deformable bar element can also be caused, which bends the bar element and lifts it out of the plane of the covering elements. In all cases, deformation of the bar elements forms a hood, that is, a cavity, in such a way that, due to the connection between the bar element and the covering element, the covering element in this area is lifted out of the original plane of the covering element together with the bar element. The reference means can then be accommodated in this cavity formed beneath the area of the covering element.

The shortening means can have first fastening means, which interact with the second fastening means on the covering element. The second fastening means on the covering element can also be formed by the covering element itself, for example, if the covering element is a film element and the shortening means is itself an adhesive ribbon-shaped element or contains adhesive areas. Separate second fastening means are then not necessary. The first fastening means can then be adhesive fastening means, for example, an adhesive coating on one side of the shortening means. Alternatively, separate second fastening means can also be attached to the covering element, in particular in the form of adhesive elements or loop and hook fastening elements. These loop or hook fastening elements can interact with matching hook or loop fastening elements as first fastening means of the shortening element.

Hook-and-loop fastening elements are often also termed Velcro fasteners, burr fasteners, or touch-and-close fasteners.

For example, the shortening means can be provided with first fastening means over its entire length. In this way, it is advantageously possible to fix the shortening element on the second fastening element in any steps, depending on the point of the shortening means at which the latter is connected with the second fastening elements.

The shortening element especially preferably consists of a textile one- or two-sided fleece-like element so that this constitutes a loop fastening element as first fastening means and, in particular, a strip or ribbon-shaped material can be used that can be connected to two or more hook fastening elements as second fastening means, which are, in particular, attached to the drape in the form of rectangular and square elements. The corresponding second fastening elements in the form of hook fastening elements are preferably disposed in the area of the bar ends in the case of non-deformed bars. In particular, in the case of elastically deformable bar elements, the deformation can advantageously be individually set due to the stepless shortening of the distance between the two hook elements, the shortening means being constituted as fleece-like material over their entire length.

Alternatively, first fastening means can also be provided only in individual regions on the shortening means, in particular, preferably only in the end areas of the shortening means. Basically, the greater the deformation and the associated arching of the bar elements, the further the area formed thereby is lifted out of the plane. At the same time, the extent of the area in the plane is reduced.

At least one of the ends of one or more shortening means can be detachably connected to the covering element, in particular, by its first fastening means to the second fastening means on the covering element. In particular, the shortening means can be detachably connected to the covering element in both end areas. In particular, the shortening means is detachably connected at its two ends by its first fastening element to the second fastening element on the covering element. Further, alternatively, the shortening means can be permanently and non-detachably connected to the covering element in one end area and only contain first fastening means in its second end area or over its remaining and partial length.

In an alternative embodiment, one or more shortening means can be included with the covering element but not attached so that the former can be attached to the second fastening element(s) individually based on the requirements.

Preferably, at least two second fastening means can be provided for each shortening means. In principle, three or more second fastening means are conceivable.

The second fastening elements are preferably provided in the region of the bar ends on the covering element. Preferably, the second fastening means in the area of the bar ends of the bar means are disposed on their outward facing side, that is, the side facing the side edges of the drape.

The second fastening elements are preferably permanently and non-detachably connected to the covering element.

According to the invention, two bar elements are provided that can include the area for accommodating the reference means between them, wherein, in particular, a shortening means is allocated to each of the bar elements.

Further bar elements can advantageously be provided, in particular, preferably three or four bar elements.

Further bar elements are advantageous, in particular, in the case of formation of an area with larger dimensions, in particular, with a larger longitudinal extent, for stabilization of this area, which is lifted out of the plane of the covering element.

In the case of more than two bar elements, it is advantageous to allocate a shortening means to each of the outermost bar elements, in particular, on their outward facing side, that is, the side facing the side edges of the drape.

The bar elements are preferably disposed parallel to each other. The distance of the bar elements from each other depends on the size of the required hood, that is, on the size of the area that is required for a reference means for a navigation system, the reference means protruding from the plane of the covering element. If more than two bar elements are provided, all bar elements can preferably be parallel. In particular, in this case, the bar elements can have different lengths even if only two bar elements are provided. In particular, if there are more than two bar elements, the groups of bar elements arising with a parallel configuration that include the area for accommodating the reference means between them can be constituted such that the bar elements with the greatest longitudinal extent are disposed within the shorter bar elements of a group. This improves the stability of the area for accommodating the reference means.

However, the bar elements can also be disposed in a non-parallel configuration, in particular two ends of the bar elements can have a smaller distance between them than the two other bar elements so that the area formed between them is not rectangular, as it is with a parallel configuration, but either triangular, if the bar ends of the two bar elements touch, or trapezoidal, if the bar ends are spaced.

The covering element preferably comprises at least partially translucent, in particular, transparent material. In particular, the area for accommodating the reference means is made of a translucent, in particular, transparent material. Further preferably, the covering element can consist completely of a translucent, in particular transparent material. Constitution of the covering element, or at least of the area, of translucent, in particular transparent material, as a film is especially preferred.

Constitution at least of the area for accommodating the reference means as translucent, in particular, transparent material, in particular as translucent, in particular, transparent film is advantageous because the reference means accommodated in this area can be directly recognized by medical personnel, which improves verification and therefore safety during an intervention on the patient.

Further, the translucent, in particular, transparent material, in particular, the translucent, in particular, transparent film preferably allows infrared with a wavelength of 780 nm to 1 mm, further, in particular, with a wavelength of 780 nm to 3000 nm and further, in particular, with a wavelength of 780 nm to 1400 nm to pass through it.

The film comprises, in particular, polymer materials from the group polyethylene (PE), polypropylene (PP), polyamide (PA), polyester (PET) and combinations thereof. The films can consist of mixtures and/or composites of the above materials. In particular, a film made of a polypropylene material and/or polyethylene material is preferred.

In particular, a film is preferably used that has a thickness of less than 200 µm, in particular, of less than 150 µm and, in particular, of less than 100 µm.

According to the invention, the bar elements are deformable. The bar elements can be wire elements or elements encasing metal. The bar elements can in particular be plastic bars or plastic-coated bars.

The length of the bar elements is preferably at least 20 cm, further preferably at least 30 cm, further preferably at least 40 cm, further preferably at least 50 cm, in particular, preferably no more than 100 cm, further preferably no more than 90 cm, further preferably no more than 80 cm.

The width of the bar elements is preferably at least 0.5 cm, further preferably at least 0.8 cm, in particular, no more than 3.5 cm, further preferably no more than 3.0 cm, further preferably no more than 2.5 cm, further preferably no more than 2.0 cm.

In the configuration of the at least two bar elements, the distance between the directly adjacent bar elements is preferably at least 10 cm, further preferably at least 20 cm, further preferably at least 25 cm, further preferably at least 30 cm, in particular, preferably no more than 80 cm, further preferably no more than 60 cm, further preferably no more than 50 cm, further preferably no more than 40 cm.

The distance between the bar elements is measured within the edges aligned with each other of each pair of directly adjacent bar elements when they are in the non-deformed condition or have been restored to their original non-deformed condition. In the case of non-parallel configuration of the bar elements, preferably both the larger and the smaller distance are within the limits stated above. In the case of more than two bar elements, if two groups of bar elements are formed, the distance between the groups can preferably be in the range stated above.

With this distance, a hood can advantageously be provided by deformation of the bar elements under which most reference systems (reference means) can be accommodated and wherein the area provided between the bar elements is an obstacle-free area for the navigation function, for example, scanning, without an excessive distance resulting in a non-stabilized, and therefore disadvantageous, sagging of the covering element.

It is basically also possible to equip the bar elements with articulations such that, as the distance between the bar ends is reduced, the bar elements are not deformed in an arch shape over their entire length, but the bar elements are bent at their articulations in such a way that, for example, a tent-shaped hood is formed if there is one articulation per bar element or, for example, cuboid-shaped hood is formed if there are two articulations per bar element.

Further, the covering element can partially also comprise non-film-like materials or be constituted by non-film-like material, wherein these non-film-like materials are, in particular, not translucent or not transparent. For these non-film-like materials, preferably nonwoven materials, in particular, spun nonwovens and/or meltblown nonwovens are used.

The covering material can preferably partially comprise nonwoven materials and nonwoven-film laminates and nonwoven-film-nonwoven laminates or be partially formed by these. In particular, however, at least the area for accommodating a reference means for a navigation system, the reference means protruding out of the plane of the covering element, can be constituted by a translucent or transparent material, in particular, a translucent or transparent film. The two materials can then be connected, for example, by a welding method. However, other connection methods, such as adhesive methods and sewing methods are conceivable.

Constitution of the entire covering element from a uniform film material is, however, especially preferred.

The surgical drape is advantageous when used as a neurosurgical drape and it is used for this purpose.

Neurosurgery is understood to mean surgical invention in the region of the spinal column and/or the head.

The surgical drape is also advantageous when used in other regions, in which reference means for navigation systems are used. For example, use in orthopedic applications is also conceivable, for example, when inserting implants in the form of endoprostheses.

Sterilization of the drape is also intended, wherein this can usually be achieved, for example, using gamma radiation. Alternatively, however, ethylene oxide sterilization or another method known in the art can also be used for sterilization.

The surgical drape is advantageously a drape that is already supplied in sterile form by the manufacturer.

In particular, the surgical drape is advantageously supplied in a folded condition by the manufacturer.

In particular, the surgical drape is advantageously folded in such a way that the area, formed between the at least two bar elements, that is intended to accommodate reference means is largely free of folds.

In the case of long, in particular plastically deformable bar elements, these bar elements for folding the surgical drape are advantageously only bent once and thus folded back upon themselves. In this way, the covering element has only one fold in the area for accommodating reference means.

In particular, the surgical drape is advantageously supplied as a sterile package by the manufacturer.

BRIEF DESCRIPTION OF THE DRAWING

Further advantages and characteristics of the invention can be derived from the remaining documents. The invention is explained in more detail by means of the drawing below. The figures show.

DESCRIPTION OF THE PREFERRED EMBODIMENT

Figure 1:
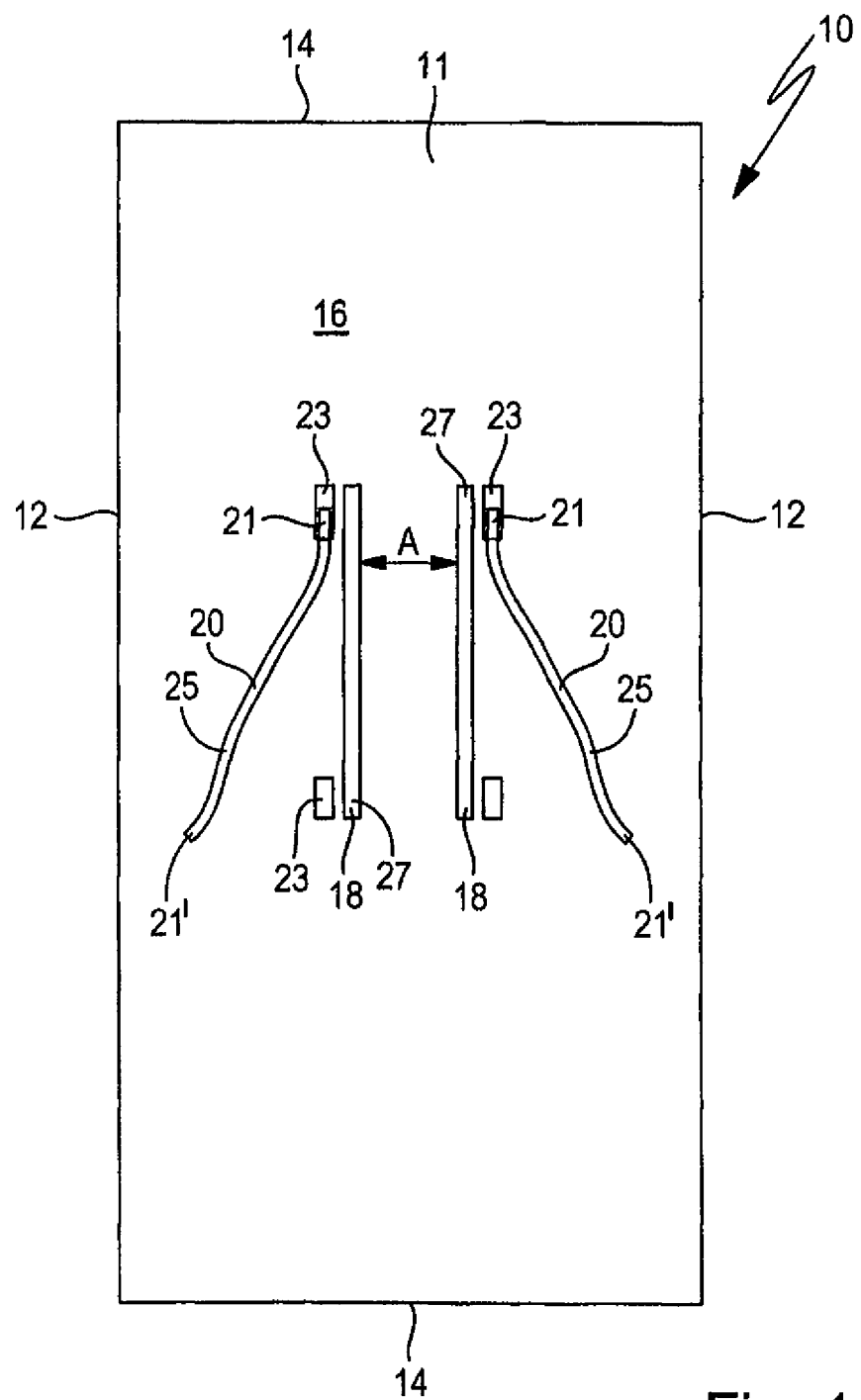
FIG. 1 a drape according to the invention with non-deformed bar elements.

FIG. 1 shows a drape that is collectively designated by reference sign 10. The drape comprises a planar, flexible covering element 11, which has a rectangular shape and in particular two longer side edges 12 and two shorter side edges 14, wherein the longer side edges 12 are to be referred to as longitudinal edges and the shorter side edges 14, as transverse edges.

The flexible and planar covering element 11 has a surface that faces a patient during use and would form the lower side in the drawing plane, as well as a side facing away from the patient that is designated by reference sign 16 and is the side facing upward in the illustration. The covering element 11 comprises a transparent film material, in particular, a polyethylene film.

Parallel with the side edges 12, two bar elements 18 are provided that also extend parallel to each other and are non-detachably connected to the drape over their entire length, for example, firmly fixed by means of an adhesive. The distance of the bar elements 18 from each other, designated by the reference sign A here, depends on the size of the required hood, that is, on the size of the area that is required for a reference means for a navigation system, the reference means protruding from the plane of the covering element 11.

Moreover, the drape comprises two shortening means, which are designated by the reference sign 20, wherein one shortening means 20 is allocated to each bar element 18 and interacts with it. The shortening means 20 are detachably fixed at one of their end areas 21 to a second fastening means 23. The shortening means 20 is constituted by a fleece-like material that constitutes a first fastening element of a hook-and-loop fastening element. The first fastening means 25 thus extend over the entire length and surface of the shortening means 20.

The second fastening means 23 are formed by so-called hook fastening elements of a hook-and-loop fastening material and are, in particular, disposed in the area of the bar end 27. The second fastening means 23 are located next to the bar ends 27 and, in particular, parallel therewith if they are rectangular fastening means 23, and also outside the area between the bar elements 18.

As has already been explained, the shortening means 20 is fixed at one of its end areas 21 to one of the second fastening means 23. The first end 21 is detachably fixed to the second fastening means 23. The second end 21' of the shortening means can be free, that is, not connected to the second fastening means 23 and, if the shortening means 20 are long enough, also connected to the second fastening means 23, without having resulted in shortening and arching of the bar elements 18 before use and hood formation in the storage position depicted.

Figure 2:
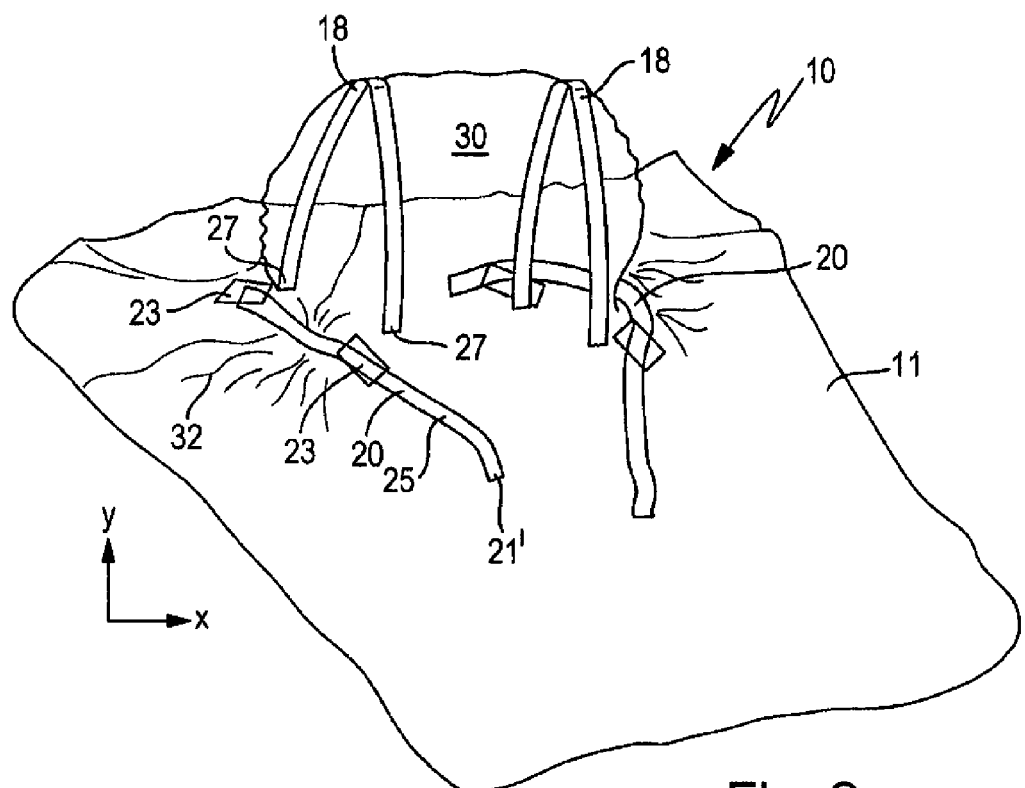
FIG. 2 the drape according to FIG. 1 with deformed bar elements.
Figure 3:
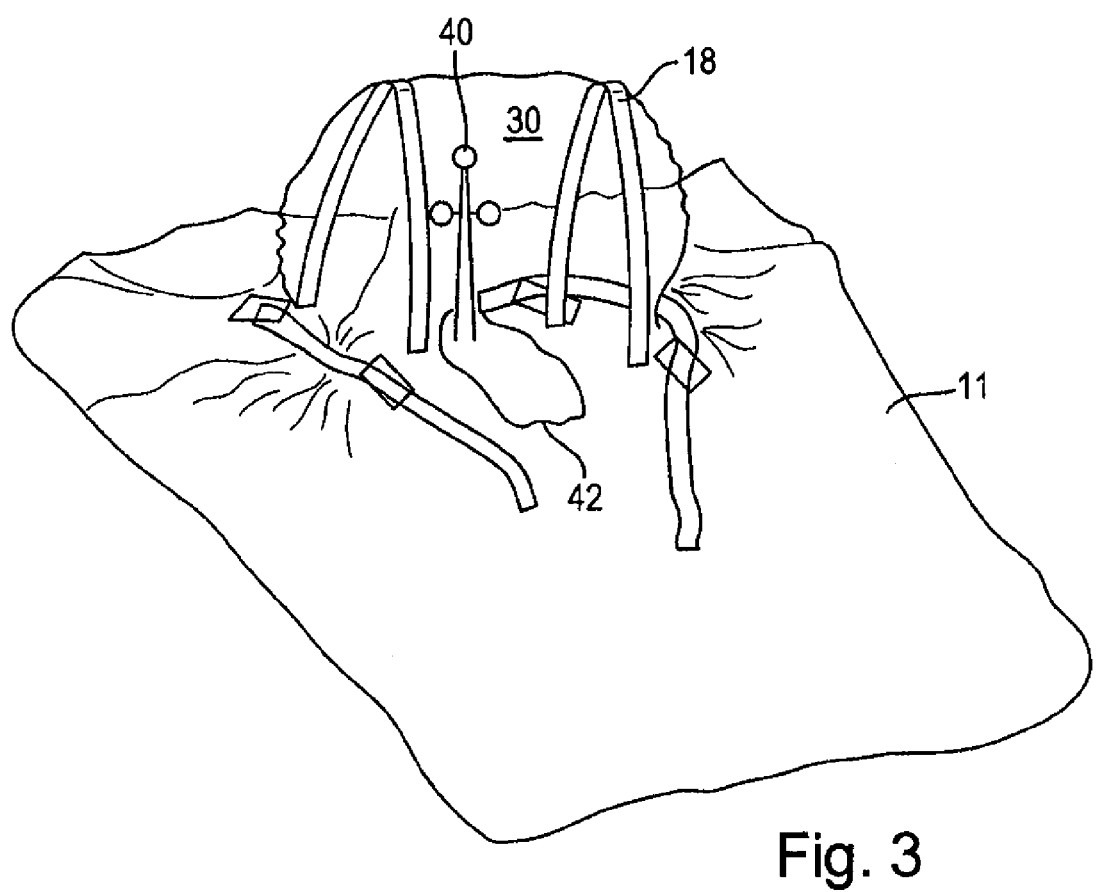
FIG. 3 the drape according to FIG. 2 with reference means in place.

FIG. 2 shows an application case in which an area 30 for accommodating a reference means for a navigation system shown in FIG. 3, the reference means protruding from the plane of the covering element, has been formed protruding from the plane.

Both bar elements 18 are to be deformed into the shape of an arch by the application of force so that the end areas 27 (bar ends) of the bar elements 18 are brought closer together in the plane of the covering element 11 and the distance between the bar ends 27 of a bar element 18 in the plane of the covering element 11 is reduced. This results in arching of the bar elements 18 out of the plane, designated by X-Y here, of the covering element 11. Because the two bar-shaped elements 18 are arched to an equal degree, an area 30 is constituted between them that has the shape of a tunnel and is lifted above the plane. Since the bar elements 18 and the covering element 11 are permanently connected to each other, the covering element 11 is also lifted out of its original plane X-Y in this area 30. The shortening means 20 are fixed to both second fastening elements 23 for each bar element 18. Outside the shortening means 20, folds 32 are formed by the material of the covering element 11. Within the area 30, however, the material of the covering element 11 remains free of folds so that the navigation system is not disturbed.

Because the shortening means 20 are constituted by fleece-like material over their entire length and therefore as a first fastening element 25, fastening of the shortening element to the second fastening element can be effected in any steps, depending on the point of the shortening means at which the latter is connected to the two fastening elements 23. The greater the deformation and therefore the arching of the bar element 18, the higher the area 30 that is lifted out of the plane. At the same time, the extent of the area 30 in the plane is reduced.

The best possible geometry must be determined for the specific reference system to be used.

FIG. 3 shows an embodiment corresponding to FIG. 2, wherein the reference means 40 is also shown that is fixed to a patient and extends out of an opening 42 on the patient into the hood-like area 30 of the covering element 11.

The bar elements 18 are plastically deformable plastic bars that are connected to the covering element 11 over their entire length.

The especially advantageous aspect of this embodiment is that a corresponding surgical drape 10 in an unused condition, as shown in FIG. 1, does not extend outside the plane direction and can thus, in particular, be folded to a dimension that corresponds to the length of the bar elements 18, ensuring easy storage. The smaller storage volume also makes sterilization easy.

During use, a corresponding area 30, which can also be referred to as a hood, can be formed simply and quickly, wherein the extent of the hood 30 can be flexibly chosen by deformation of the bar elements and by setting and/or stabilization using the shortening means 20.

In this way, a fold-free hood 30 can also be formed so that an appropriate navigation system, comprising a camera, in particular, can sense the reference means 40 without being disturbed by reflections. In particular, the covering element 11 is a film material that is designed to allow infrared to pass through it. If the result of an operation is intraoperatively verified, for example, by means of a computer tomograph or a C-arm, navigation such as is commonly practiced today can be performed with a system in which a camera system can track the reference means 40, for example, a reference star, which is fixed in the opened body of the patient. This camera system should also be able to work during the computer tomography and X-ray procedure to detect every change and disturbance immediately.

I claim:

1. A surgical drape, the surgical drape structured to accommodate a reference element for a navigation system, the surgical drape comprising:
    a planar, flexible covering element having an area for accommodating the reference element, the reference element thereby protruding from a plane of said covering element;
    at least two deformable, elongated bar elements which are at least partially connected to said covering element, each of said bar elements having two bar ends, wherein said area for accommodating the reference element is disposed between said bar elements; and
    at least one elongated shortening element, said elongated shortening element structured to be fixed to said covering element and to interact with at least one of said bar elements, thereby reducing and/or fixing a distance between two bar ends in said plane of said covering element, said area for accommodating the reference element thereby being lifted out of said plane of said covering element.

2. The surgical drape of claim 1, wherein said shortening element has a first fastening element, which interacts with a second fastening element on said covering element.

3. The surgical drape of claim 2, wherein said shortening element is constituted to have said first fastening element over an entire length thereof.

4. The surgical drape of claim 2, wherein at least two fastening elements are provided for each shortening element.

5. The surgical drape of claim 2, wherein said second fastening element is provided on said covering element, at least in an area of said bar ends.

6. The surgical drape of claim 2, wherein said first fastening element is connected to said second fastening element on said covering element.

7. The surgical drape of claim 2, wherein said first fastening element is a loop fastening element of a hook-and-loop fastening material and said second fastening element is a hook fastening element of a hook-and-loop fastening material.

8. The surgical drape of claim 1, wherein at least one shortening element is allocated to each of said bar elements.

9. The surgical drape of claim 1, wherein said two bar elements are disposed parallel to each other.

10. The surgical drape of claim 1, wherein at least one end of said at least one shortening element is detachably connected to said covering element.

11. The surgical drape of claim 1, wherein one end of said at least one shortening element is permanently and non-detachably connected to said covering element.

12. The surgical drape of claim 1, wherein a distance between said two bar ends of said bar element can be shortened and fixed continuously.

13. The surgical drape of claim 1, wherein a distance between said two bar ends of said bar element can be shortened and fixed in defined positions.

14. The surgical drape of claim 1, wherein said area of said covering element is constituted by a translucent material.

15. The surgical drape of claim 14, wherein said area of said covering element is constituted by a translucent film.

16. The surgical drape of claim 1, wherein an entire said covering element is constituted by a translucent material.

17. The surgical drape of claim 16, wherein said entire covering element is constituted by a translucent film.

18. The surgical drape of claim 1, wherein said area of said covering element is constituted by a transparent material.

19. The surgical drape of claim 18, wherein said area of said covering element is constituted by a transparent film.

20. The surgical drape of claim 1, wherein an entire said covering element is constituted by a transparent material.

21. The surgical drape of claim 20, wherein said entire covering element is constituted by a transparent film.

22. The surgical drape of claim 1, wherein the drape is structured and dimensioned for use as a neurosurgical drape.

* * * * *